Figure 1:
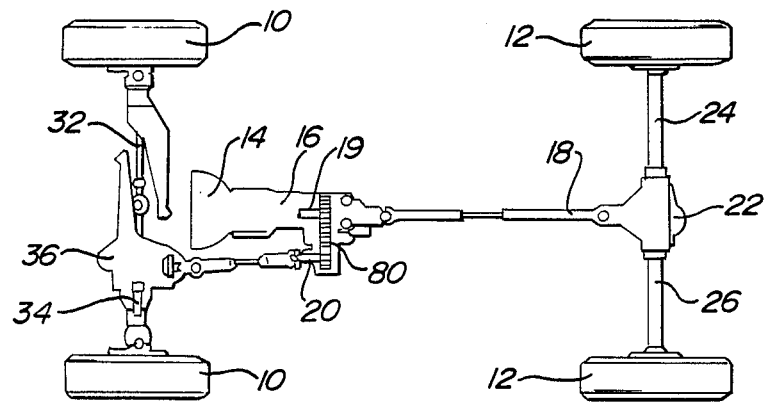

United States Patent [19]

Sulc et al.

[11] Patent Number: 4,963,148
[45] Date of Patent: Oct. 16, 1990

[54] INTRAOCULAR OPTICAL SYSTEM

[75] Inventors: Jiří Šulc; Krčová Zuzana, both of Prague, Czechoslovakia

[73] Assignee: Ceskoslvnska akademie ved, Prague, Czechoslovakia

[21] Appl. No.: 331,435

[22] Filed: Mar. 31, 1989

[30] Foreign Application Priority Data

Apr. 11, 1988 [CS] Czechoslovakia ............... 2470-88

[51] Int. Cl.$^5$ ............................................. A61F 2/16
[52] U.S. Cl. ................................................. 623/6
[58] Field of Search .......................................... 623/6

[56] References Cited

U.S. PATENT DOCUMENTS

| | | | |
|---|---|---|---|
| 4,253,199 | 3/1981 | Banko | 623/6 |
| 4,704,122 | 11/1987 | Portnoy | 623/6 |
| 4,731,079 | 3/1988 | Stoy | 623/6 |
| 4,731,080 | 3/1988 | Galin | 623/6 |
| 4,790,847 | 12/1988 | Woods | 623/6 |
| 4,813,954 | 3/1989 | Siepser | 623/6 |
| 4,842,601 | 6/1989 | Smith | 623/6 |

Primary Examiner—Ronald Frinks
Attorney, Agent, or Firm—Leydig, Voit & Mayer

[57] ABSTRACT

The solution pertains to an intraocular optical system consisting of a hollow elastically deformable insert (7), following the shape of capsula lentis (6) at least in main lines, leaning against the inner wall of capsula lentis and keeping it moderately tensioned, which insert (7) consists of a front element (1) and rear element (2) and an elastic element (3) placed between them, may be provided with openings (9) allowing the flow of liquid, and contains one to four lenses (4,5) placed in the main axis of eye, whereas at least one of these lenses is connected with the insert (7) in such a way, that it moves axially at the contraction and release of accommodation muscles and thus changes its position between the retina and cornea.

The insert (7) is made from biocompatible materials as are silicone elastomers, hydrogels, advantageously elastic and with the shape memory, for example, from partially dried hydrogels with the hydrophilized surface, or from material with the glass-transition temperature $T_g$ from $-5°$ C. to $45°$ C. or with $T_g$ adjusted to meet this requirement, for example, by swelling hydrogels into a non-equilibrium state. The insert (7) deformed into a rod-like form with the diameter less than 3 mm can be introduced into an eye through a very small incision.

23 Claims, 3 Drawing Sheets

INTRAOCULAR OPTICAL SYSTEM

The invention pertains to an intraocular optical system.

Intraocular lenses, above all the hard lenses from poly(methyl methacrylate), inserted into capsula lentis after removal of natural lens, usually as a consequence of cataract, reached a considersble perfection but still have some shortcomings. Some of them, for example, the tendency to the growth of cells on the surface of lenses and irritation of living tissues, above all in the places of the contact of suppporting projections (haptics), and the tendency to from strong light reflexes, could be removed by a surface hydrophilization in such a way that a soft surface layer with the swelling gradient is created, but the shortcoming consisting in the necessity to make a long incision at operation still remains unsolved.

A considerable improvement of this state is brought by a soft intraocular lens based on the hydrophilic gels according to the U.S. Pat. No. 4,834,753 to Sulc, et al. which in its deformed shape enables to insert the lens to the preserved capsula lentis through a small incision, where the lens assume its correct shape and required position.

A disadvantage of soft intraocular lenses based on hydrophilic gels used so far in comparison with the original natural lens consists in a difficult accommodation to various distances, especially in elderly patients. This is given by the fact, that hydrogels need larger powers for deformation than can be developed by the pertinent eye muscles. Very soft lenses have a low refractive index of light, low strength, and large volume, which may develop so called secondary glaucoma due to clogging of natural passages.

An objective of the present invention is an intraocular optical system for insertion into capsula lentis after removal of natural lens, which system consists of a hollow elastically deformable insert 7 following the shape of capsula lentis 6, at least in main lines, leaning against the inner wall of capsula lentis and keeping it in a moderately tensioned state, which insert is formed by a front element 1 and rear element 2 and an elastic element 3 placed between them, may be provided with openings 9 allowing the flow of liquid, and contains one to four lenses 4, 5 placed in the main axis of eye, whereas at least one of these lenses is connected with the insert 7 in such a way, that it moves axially at the contraction and release of accommodation muscles and thus changes its position between the retina and cornea.

At least one of the lenses may be placed in the optical system concerned outside the geometric center of insert and capsula lentis.

The insert 7 can be made from various biocompatible materials, for example, from silicone elastomers, hydrogels, and the like, which are advantageously elastic and have the shape memory, for example, partially dried hydrogels, and may be hydrophilized on the surface.

The insert 7 can be inserted into an eye through a small-incision, i.e. smaller than 3 mm, in a deformed state if it is formed from a material with the glass-transition temperature $T_g$ between $-5°$ C. and $45°$ C. or if its $T_g$ is adjusted before implantation in such a way that it meets the above condition, for example, by swelling the hydrophilic gels into a non-equilibrium state.

The insert 7 is then heated above the glass-transition temperature, deformed into a rod-like shape with diameter smaller than 3 mm, and cooled below this temperature retaining its rod-like shape. After insertion into an eye, the insert spreads into the original shape due to the body temperature. The lenses of optical system can be inserted into an eye in the same way.

The intraocular optical system according to the invention enables to use the lenses from an arbitrary material, i.e. not only from hydrogel but also from hard acrylic polymers as is poly(methyl methacrylate), without the known shortcomings, such as irritation of neighboring tissues, become operative. On the contrary, the application of hard lenses with a high refractive index enables to reduce their dimension in such a way that the posterior chamber of eye remains unfilled and the whole system fits into the original capsule lentis from which the natural turbid lens was removed, for example, by phacoemulsification.

It is of advantage, if at least one of the lenses placed in the insert 7 is made of a synthetic polymer with refractive index of light at least 1.336.

The insert 7 may have the shape of a rotation ellipsoid provided on its circumference with an equatorial slot with a row of holes 9 and may be provided on its front side 1 with an opening which has a smaller diameter than has the opening in the capsule lentis 6.

The front part and back part of the insert may be realized as rings with diameter less than 9 mm or as parts of hollow rotation bodies as are sphere, paraboloid, ellipsoid, and the like, or also lenses (optical elements) may be included as their parts, whereas the lenses and their case may form a single piece. The elastic element 3 may have the shape of fibers, strips, spiral, or corrugated body.

The lens 5 may be fixed either in the rear part 2 or front part 1 of the elastic insert 7 or, if two lenses 4, 5 are used, in both parts. In the latter case, both lenses move away one from another at the accommodation for near sight and approach one another at the accommodation for a long-distance sight. In addition to this, the whole system may be complemented by insertion of further intraocular lens or lenses into the elastic insert 7. It is important that the accommodation proceeds only by shifting the substitute lens in the eye axis forwards and backwards similarly as in photographic cameras and not by changing the shape of lens as it is in a healthy eye, where the shift of lens in the eye axis is smaller and occurs parallel with the change in its curvature, i.e. with the change in its optical power. The so called zoom effect, which takes place in a healthy eye during accommodation to a smaller extent, may be also attained with the system according to this invention with two or more lenses, without parallel change in the optical power of individual lenses.

Various performances of the intraocular optical system according to the invention are diagrammatically shown in the appended FIGS. 1 through 6.

FIG. 1 shows a section of the intraocular optical system which consists of the insert 7 containing the front part 1, elastic element 3 realized in the shape of an equatorial slot provided with holes 9 on the circumference, and rear part 2 which component is the lens 5. The intraocular lens 4 is inserted into the front part of the insert 7. The whole system is placed in the capsula lentis 6.

Figure 2:
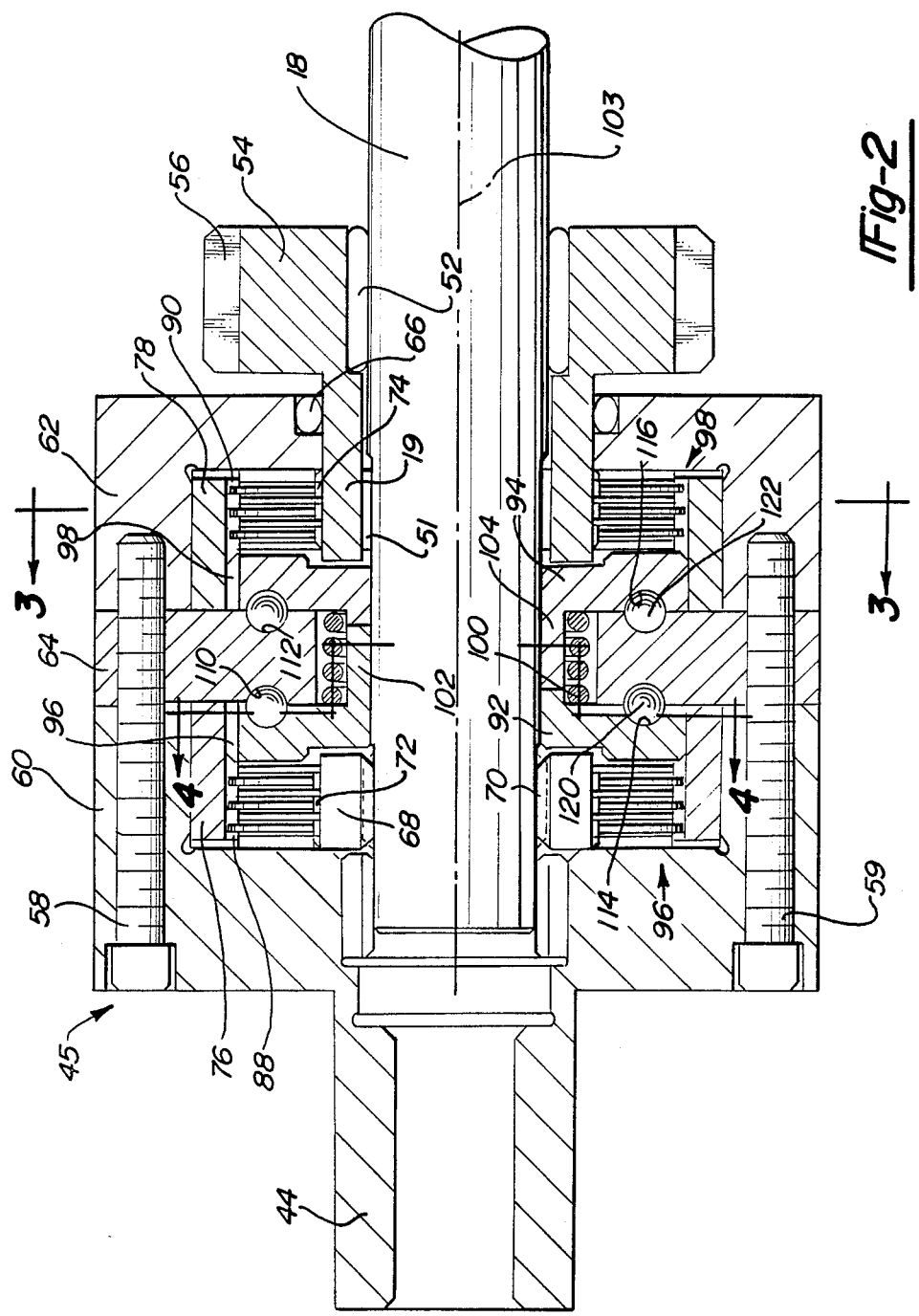

FIG. 2 shows the same cross-section viewed from above.

Figure 3:
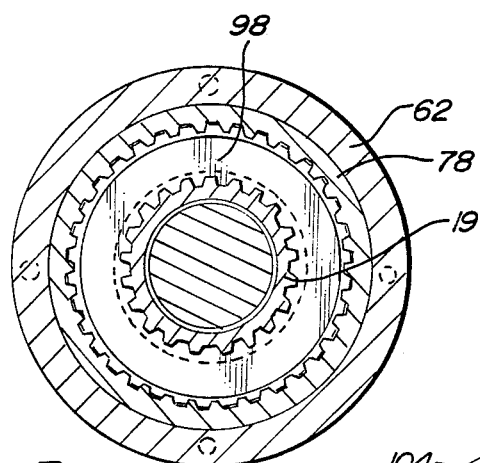
Figure 7:
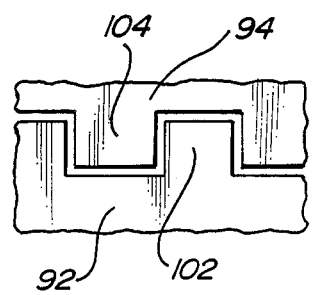

A sectional view on the intraocular system is in FIG. 3, in which the front part 1 with the lens 5 and the rear part 2 with the lens 4 are connected with the elastic element 3 realized as a spring.

Figure 4:
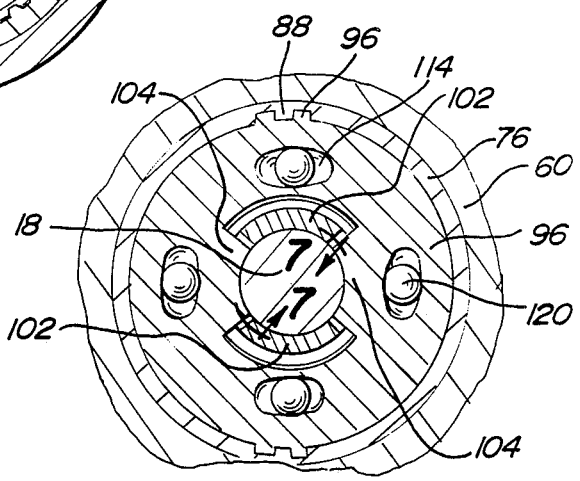

FIG. 4 presents a section through the intraocular optical system, where the front part 1 and rear part 2 of the insert 7 are created as rings connected with the elastic element 3 forming elastic ring. The lens 4 and 5 are inserted into inner slots. The whole system is placed in the capsula lentis 6.

Figure 5:
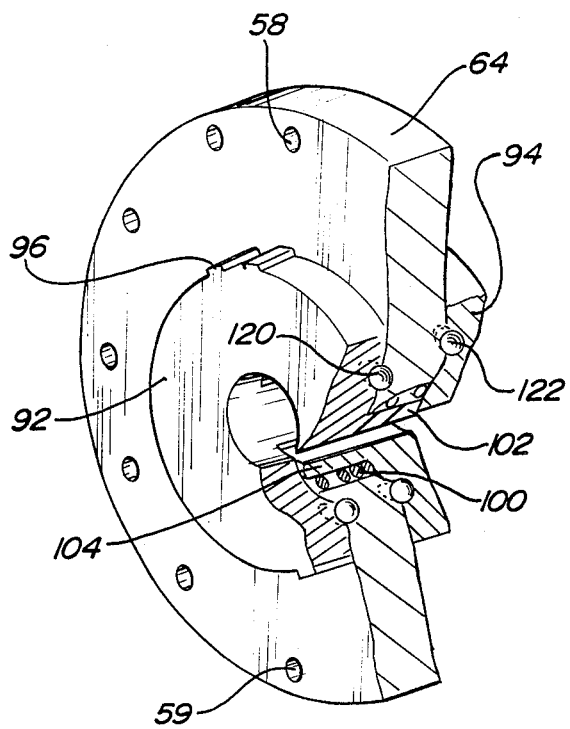

The intraocular optical system, which sectional view is shown in FIG. 5, consists of the insert 7 from the front part 1 and the rear part 2 having the shape of a part of ellipsoid and the elastic part 3 formed as an equatorial slot provided with a row of holes 9. The lens 5 is inserted into the front segment.

Figure 6:
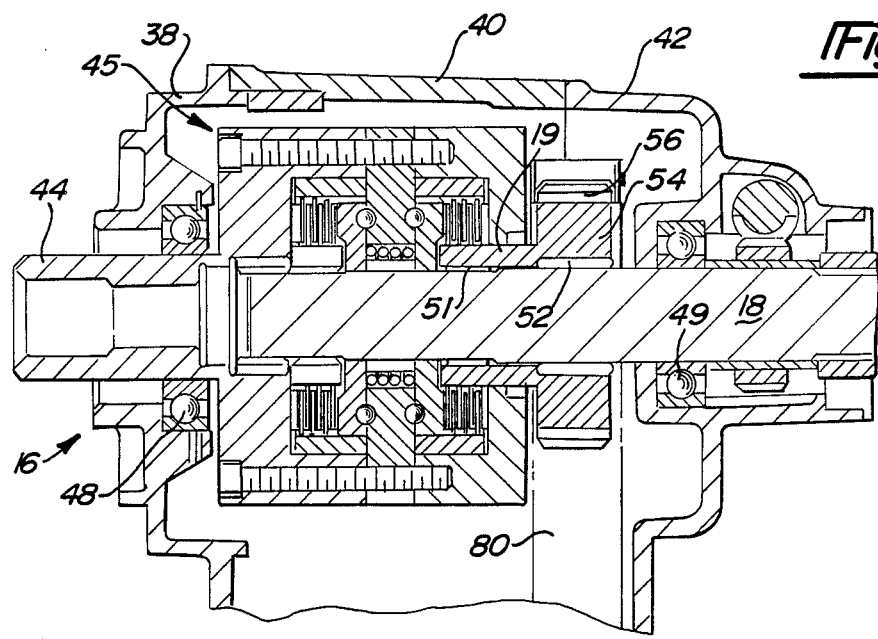
Figure 1:
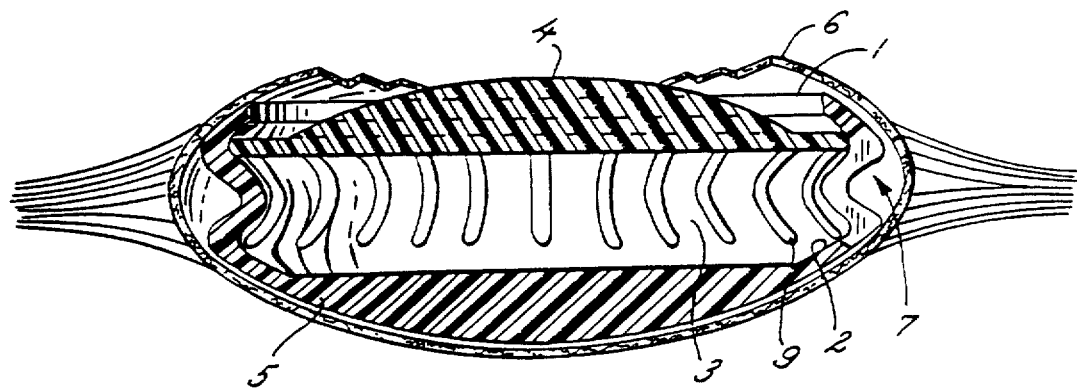
Figure 2:
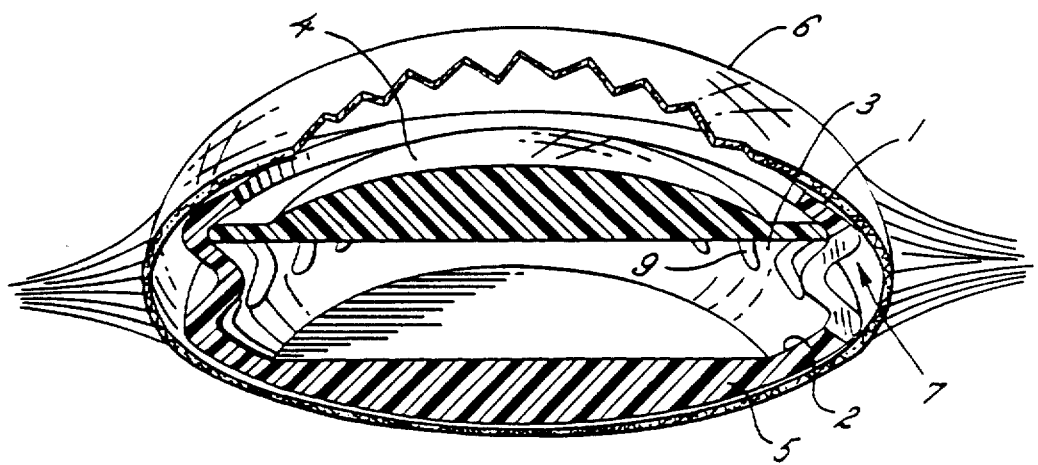
Figure 3:
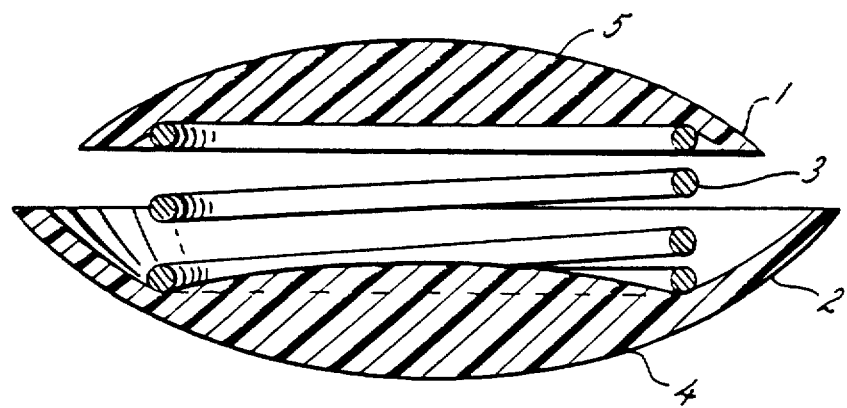
Figure 4:
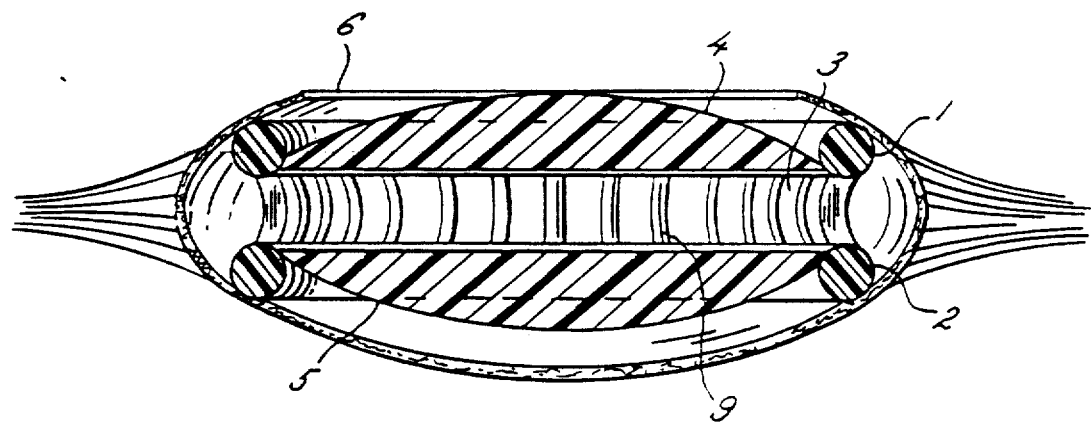
Figure 5:
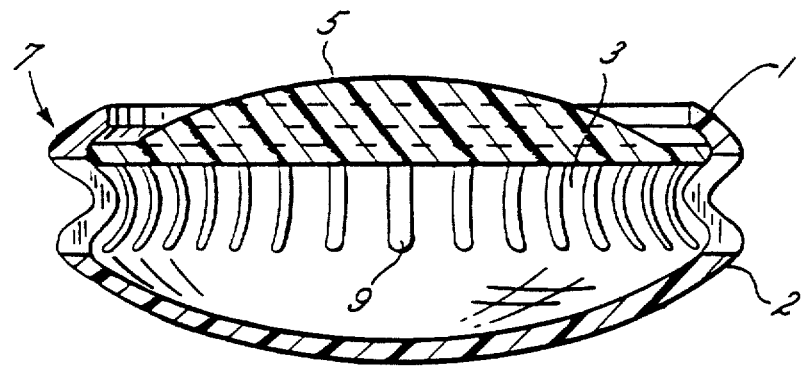
Figure 6:
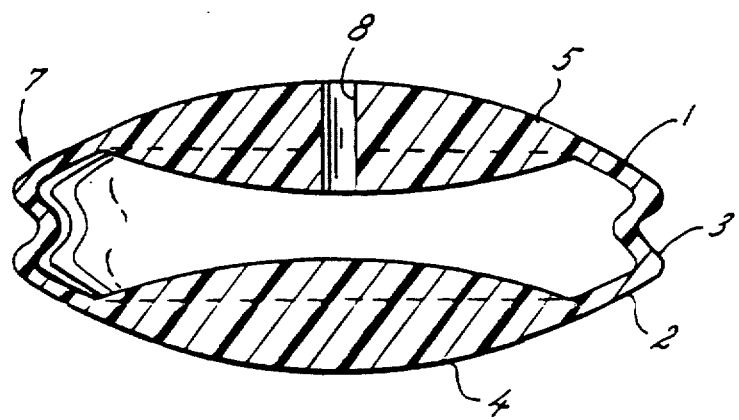

FIG. 6 shows a section of the intraocular system, where the lenses 4, 5 (optical elements) and the insert 7 are monolithic and from a single piece. The hole 8 in the central part of front lens 5 enables the circulation of chamber liquid.

As follows from the drawings, the insert 7 from an elastic and easily deformable material may be provided with central opening, in the front, back, or both sides, or with the equatorial slot with a row of holes letting liquids through, or with a combination of both provisions. The elasticity of the very insert 7 may be replaced or complemented with a centrically placed spiral spring 3 or elastic connection elements 3, where liquids can flow in between. The lens 4 or 5 or the lenses 4, 5 may be fixed in the rear part 2 or front part 1 of the insert 7 or in both parts, or may be held in the eye axis by radial or oblique fibers. The oblique fibers are longer than the straight radial fibers and may be therefore easily elastically stretched.

In the most simple arrangement, the elastic insert 7 may be reduced to two rings 1, 2 connected with the elastic elements 3 and the space enabling the flow of surrounding liquid. These rings have diameter less than 9 mm and the elastic connecting elements may have the form of fibers, strips, spiral or corrugated body so that the capsula lentis is moderately and uniformly tensioned by the said rings. The rings may be replaced with parts of hollow rotation bodies as a sphere, paraboloid, ellipsoid, and the like. They may be made from various biocompatible materials, advantageously elastic material with the shape memory, for example, partially dried hydrogels which may be hydrophilized on the surface, for example, by partial hydrolysis or sulfonation, which may be completed with a partial surface esterification with multifunctional alcohols containing, even after crosslinking esterification, additional free hydrophilic groups, silicone composite, and the like.

It is advantageous to provide an opening in the front part of the insert, which is larger than is the hole in the front part of capsula lentis formed at the extraction of natural lens. The non-uniform edges of the hole are not mechanically stressed in this way.

The insert 7 and/or the lens 4, 5 may contain a drug in their material, which is released after implantation. Such a drug may be cytostatic or antibody liquidating cells on the inner wall of capsula lentis which cause a secondary cataract by producing the lens materials, corticoids, antibiotics, and the like. These drugs disappear after certain time.

The lenses 5 placed in the front part 1 of the insert 7 may be provided in the center with a hole of 0.05 to 1 mm which enables a better communication between the anterior and posterior chamber of eye and prevents from the formation of secondary glaucoma. This hole does not affect the optical quality of image.

The insert 7 of the intraocular optical system may be manufactured in various ways similarly as the lenses, viz. by turning, rotation casting, or dipping.

It is advantageous to prepare the insert 7 in a similar way that the intraocular lens according to the Czechoslovak Patent Application PV 9596-86, so that its glass-transition temperature $T_g$ is from $-5°$ C. to $45°$ C., the insert is deformed at the temperature above $T_g$ into a form suitable for implantation and cooled in this deformed form. The insert 7, after insertion into capsula lentis 9, relaxes by postswelling and heating to the temperature of eye and thus acquires the desirable final shape.

We claim:

1. An intraocular optical system adapted for insertion into a capsula lentis after removal of a natural lens, said capsula having interior anterior and posterior surfaces, said system comprising an elastically deformable insert whose shape follows generally the interior surfaces of the capsula said insert being adapted for leaning against the interior surfaces of the capsula and keeping the capsula in a moderately tensioned state, said insert comprising a front element, a rear element, an elastic element located therebetween, and being provided with a plurality of openings in its circumference which permit the flow of liquid, and at least one lens adapted for placement along the main axis of the eye and being in communication with said insert, wherein upon insertion into the capsula said front element is adapted for communicating with substantially all of the anterior surface of the capsula and said rear element is adapted for communicating with substantially all of the posterior surface of the capsula.

2. The intraocular optical system according to claim 1, wherein at least one lens is placed outside the geometrical center of said insert and the capsula.

3. The intraocular optical system according to claim 1, wherein said elastic element is hollow.

4. The intraocular optical system according to claim 1, wherein said insert is deformed, before insertion into the eye, into a rod-like shape having a diameter of less than 3 mm.

5. The intraocular system according to claim 1, wherein at least one lens is produced from a synthetic polymer having an index of refraction of at least 1.336.

6. The intraocular optical system according to claim 1, wherein said insert has the shape of a rotation ellipsoid and is provided on the circumference with an equatorial slot having a plurality of holes.

7. The intraocular system according to claim 1, wherein the front element is provided with an opening having a smaller diameter than the diameter of the hole in the capsula.

8. The intraocular optical system according to claim 1, wherein at least one lens is fixed in the axis of said system by an elastic element which is in communication with the circumference of said lens.

9. The intraocular optical system according to claim 1, wherein said elastic element comprises subelements selected from the group consisting of fibers and strips.

10. The intraocular optical system according to claim 1, wherein said insert further comprises drugs which are releasably incorporated therein.

11. The intraocular optical system according to claim 1, wherein each lens in the optical system is provided with a hole in its center having a diameter of about 0.05 mm to about 1 mm.

12. The intraocular optical system according to claim 1, wherein said front part and said rear part have shapes selected from the group consisting of spheroids, paraboloids, and ellipsoids.

13. The intraocular optical system according to claim 1, wherein said front part and said rear part have diameters of approximately 9.0 mm.

14. The intraocular optical system according to claim 1, wherein at least one lens is in communication with said front part.

15. The intraocular optical system according to claim 1, wherein at least one lens is in communication with said rear part.

16. The intraocular optical system according to claim 1, wherein said insert is comprised of biocompatible materials selected from the group consisting of silicone elastomers which possess shape memory, hydrogels which are elastic and possess shape memory, partially dried hydrogels, the surface of said hydrogels having been hydrophilized, a material having a glass-transition temperature $T_g$ from about $-5°$ C. to about $45°$ C., and a material in which $T_g$ is adjusted to the required value before insertion into the eye.

17. The intraocular optical system according to claim 16, wherein said material in which $T_g$ is adjusted to the required value before insertion into the eye is produced by swelling hydrogels until said hydrogels reach a non-equilibrium state.

18. The intraocular optical system according to claim 1, wherein said elastic element comprises a spring.

19. The intraocular optical system according to claim 1, wherein said elastic element is corrugated.

20. The intraocular optical system according to claim 1, wherein said insert comprises a plurality of lenses.

21. The intraocular optical system according to claim 20, wherein at least a first lens in in communication with said front element and at least a second lens is in communication with said rear element.

22. An intraocular optical system adapted for insertion into a capsula lentis after removal of a natural lens, said capsula having anterior and posterior surfaces, said system comprising an elastically deformable insert, said insert being adapted for leaning against the interior surface of the capsula and keeping the capsula in a moderately tensioned state, said insert comprising an anterior ring, a posterior ring, an elastic element located therebetween which contacts the periphery of said front and rear rings and biases said rings apart from one another, and at least one lens adapted for placement along the main axis of the eye and being in communication with said insert.

23. An intraocular optical system adapted for insertion into a capsula lentis after removal of a natural lens, said capsula having anterior and posterior surfaces, said system comprising an elastically deformable insert whose shape follows generally the interior surfaces of the capsula, said insert being adapted for leaning against the interior surface of the capsula and keeping the capsula in a moderately tensioned state, said insert comprising a front element, a rear element, an elastic element located therebetween which contacts the periphery of said front and rear elements and biases said elements apart from one another, and at least one lens adapted for placement along the main axis of the eye and being in communication with said insert, wherein upon insertion into the capsula said front element is adapted for communicating with substantially all of the anterior surface of the capsula and said rear element is adapted for communicating with substantially all of the posterior surface of said capsula.

* * * * *

UNITED STATES PATENT AND TRADEMARK OFFICE
CERTIFICATE OF CORRECTION

PATENT NO. : 4,963,148

DATED : October 16, 1990

INVENTOR(S) : Sulc, et al

It is certified that error appears in the above-identified patent and that said Letters Patent is hereby corrected as shown below:

The title page should be deleted to appear as per attached title page.

The sheets of drawings should be deleted to appear as per attached sheets.

Signed and Sealed this

Fifteenth Day of January, 1991

*Attest:*

HARRY F. MANBECK, JR.

*Attesting Officer*  *Commissioner of Patents and Trademarks*

United States Patent [19]

Sulc et al.

[11] Patent Number: 4,963,148
[45] Date of Patent: Oct. 16, 1990

[54] INTRAOCULAR OPTICAL SYSTEM

[75] Inventors: Jiří Šulc; Krčová Zuzana, both of Prague, Czechoslovakia

[73] Assignee: Ceskoslvnska akademie ved, Prague, Czechoslovakia

[21] Appl. No.: 331,435

[22] Filed: Mar. 31, 1989

[30] Foreign Application Priority Data

Apr. 11, 1988 [CS] Czechoslovakia ............ 2470-88

[51] Int. Cl.$^5$ .................................. A61F 2/16
[52] U.S. Cl. ........................................ 623/6
[58] Field of Search ............................... 623/6

[56] References Cited

U.S. PATENT DOCUMENTS

| 4,253,199 | 3/1981 | Banko | 623/6 |
|---|---|---|---|
| 4,704,122 | 11/1987 | Portnov | 623/6 |
| 4,731,079 | 3/1988 | Stoy | 623/6 |
| 4,731,080 | 3/1988 | Galin | 623/6 |
| 4,790,847 | 12/1988 | Woods | 623/6 |
| 4,813,954 | 3/1989 | Siepser | 623/6 |
| 4,842,601 | 6/1989 | Smith | 623/6 |

Primary Examiner—Ronald Frinks
Attorney, Agent, or Firm—Leydig, Voit & Mayer

[57] ABSTRACT

The solution pertains to an intraocular optical system consisting of a hollow elastically deformable insert (7), following the shape of capsula lentis (6) at least in main lines, leaning against the inner wall of capsula lentis and keeping it moderately tensioned, which insert (7) consists of a front element (1) and rear element (2) and an elastic element (3) placed between them, may be provided with openings (9) allowing the flow of liquid, and contains one to four lenses (4,5) placed in the main axis of eye, whereas at least one of these lenses is connected with the insert (7) in such a way, that it moves axially at the contraction and release of accommodation muscles and thus changes its position between the retina and cornea.

The insert (7) is made from biocompatible materials as are silicone elastomers, hydrogels, advantageously elastic and with the shape memory, for example, from partially dried hydrogels with the hydrophilized surface, or from material with the glass-transition temperature $T_g$ from $-5°$ C. to $45°$ C. or with $T_g$ adjusted to meet this requirement, for example, by swelling hydrogels into a non-equilibrium state. The insert (7) deformed into a rod-like form with the diameter less than 3 mm can be introduced into an eye through a very small incision.

23 Claims, 3 Drawing Sheets

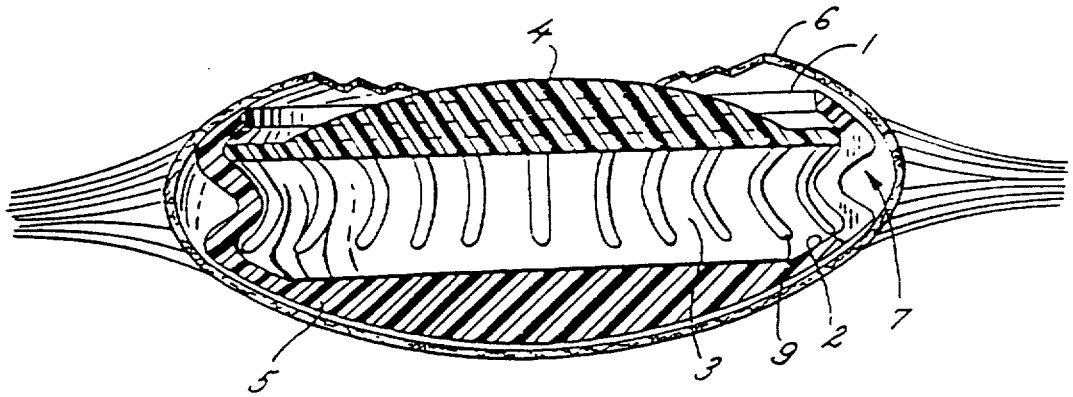

UNITED STATES PATENT AND TRADEMARK OFFICE
CERTIFICATE OF CORRECTION

PATENT NO. : 4,963,148

DATED : October 16, 1990

INVENTOR(S) : Sulc et al

It is certified that error appears in the above-identified patent and that said Letters Patent is hereby corrected as shown below:

On the title page, item [75] Inventors: change the second inventor's name to read --Zuzana Krcova--; and item [73] Assignee: delete "Ceskoslvnska" and substitute therefor --Ceskoslovenska--.

Signed and Sealed this

Seventeenth Day of November, 1992

Attest:

DOUGLAS B. COMER

Attesting Officer

Acting Commissioner of Patents and Trademarks